(12) United States Patent
Vasapollo

(10) Patent No.: US 9,943,663 B2
(45) Date of Patent: Apr. 17, 2018

(54) EROTIC DREAM INDUCTION APPARATUS

(71) Applicant: Curzio Vasapollo, Tokyo (JP)

(72) Inventor: Curzio Vasapollo, Tokyo (JP)

( * ) Notice: Subject to any disclaimer, the term of this patent is extended or adjusted under 35 U.S.C. 154(b) by 237 days.

(21) Appl. No.: 14/712,089

(22) Filed: May 14, 2015

(65) Prior Publication Data

US 2016/0331924 A1  Nov. 17, 2016

(51) Int. Cl.
*A61M 21/00* (2006.01)
*A61B 5/048* (2006.01)
*A61B 5/00* (2006.01)
*A61H 9/00* (2006.01)
*A61H 19/00* (2006.01)
*A61B 3/113* (2006.01)
*A61B 5/11* (2006.01)

(52) U.S. Cl.
CPC ............ *A61M 21/00* (2013.01); *A61B 5/048* (2013.01); *A61B 5/4812* (2013.01); *A61H 9/0078* (2013.01); *A61B 3/113* (2013.01); *A61B 5/11* (2013.01); *A61H 19/30* (2013.01); *A61H 2201/165* (2013.01); *A61H 2201/1619* (2013.01); *A61H 2201/1628* (2013.01); *A61H 2201/1654* (2013.01); *A61H 2201/5007* (2013.01); *A61H 2201/5064* (2013.01); *A61H 2205/025* (2013.01); *A61H 2205/082* (2013.01); *A61H 2205/087* (2013.01); *A61H 2230/00* (2013.01); *A61H 2230/06* (2013.01); *A61H 2230/065* (2013.01); *A61H 2230/10* (2013.01); *A61H 2230/105* (2013.01); *A61M 2021/0022* (2013.01); *A61M 2205/07* (2013.01); *A61M 2205/3569* (2013.01); *A61M 2205/3592* (2013.01); *A61M 2205/50* (2013.01); *A61M 2209/088* (2013.01); *A61M 2210/1007* (2013.01); *A61M 2210/1067* (2013.01); *A61M 2210/1475* (2013.01); *A61M 2210/16* (2013.01); *A61M 2230/04* (2013.01); *A61M 2230/10* (2013.01); *A61M 2230/18* (2013.01); *A61M 2230/63* (2013.01)

(58) Field of Classification Search
CPC ............... A61F 5/41; A61F 2005/412; A61F 2005/415; A61F 2/004; A61H 19/32; A61H 2201/165; A61H 2205/082; A61H 9/005; A61H 19/34; A61H 21/00
See application file for complete search history.

(56) References Cited

U.S. PATENT DOCUMENTS

2002/0133877 A1* 9/2002 Kuiper ................... A61G 7/001 5/81.1 R
2014/0345060 A1* 11/2014 Ribble ................... A61G 7/015 5/706

* cited by examiner

*Primary Examiner* — Christine H Matthews
(74) *Attorney, Agent, or Firm* — Russ Weinzimmer & Associates, PC

(57) ABSTRACT

An erotic dream induction apparatus includes an inflatable air bladder, such as a rubber balloon, to induce sexual arousal via genital stimulation. The air bladder is brought into contact with either the penis or vagina of the user, and/or is inserted into the anus and/or vagina of the user. In one embodiment, the air bladder is brought into contact with the penis, vagina, and/or anus of the user by being maintained in position near, against, or around the penis, vagina, and/or anus by means of straps or pockets in stimulation underwear, such that when the air bladder is inflated, the air bladder makes contact with at least a portion of the penis, vagina, and/or anus of the user. The air bladder is repeatedly inflated and deflated by pumps and/or valves.

20 Claims, 7 Drawing Sheets

EROTIC DREAM INDUCTION APPARATUS

FIELD OF THE INVENTION

This invention relates generally to sleep apparatus, more particularly to dream induction apparatus.

BACKGROUND

Most available erotic stimulators use vibration and/or a rotary motion to stimulate the user. These erotic stimulators are available in a large variety of shapes and sizes, and share several disadvantages:

the vibration and/or motion, characterized by low force and high frequency, is very different from the physical contact they are meant to simulate;

they must normally be held in place manually by the user so that the vibration and/or motion is transmitted to erogenous areas of the user's body; and the vibration and/or motion creates considerable noise.

In particular, these disadvantages make existing sexual stimulators unsuitable for use during sleep. A user may wish to utilize stimulation during sleep so as to achieve erotic dreams, as referenced in patent application WO2011132142 A1. However, the noise of vibrating motors typically used in ordinary erotic stimulators is easily transmitted and amplified through a mattress, and is sufficient to awaken the user.

Two existing types of self-stimulation devices that do not utilize motors (and therefore do not produce noise) are the Fleshlight® and inflatable dolls.

The Fleshlight® is an erotic stimulator with a handle and a soft silicone interior. The silicone interior has a hole in which the penis is inserted. This product aims to provide more realistic stimulation than a vibrating device, and it does not produce noise. However, it is a device requiring the user to actively hold and move the device to deliver the stimulation. Further, it can only be used if the user's penis is erect, and the user is awake.

Inflatable dolls (also known as sex dolls, love dolls, or blow up dolls) have the many of the same limitations as the Fleshlight® because essentially they are a Fleshlight® with an attached body, and so require active and intentional movements from the user to derive stimulation from the device.

SUMMARY OF THE INVENTION

The present erotic dream induction apparatus uses one or more inflatable air bladders, either inserted into the user's rectum and/or vagina, or held in place (typically against a user's genitalia) using straps, adhesive tape, or one or more pockets in a stimulation garment, such as stimulation underwear and/or a stimulation bra. Each air bladder is connected by a soft flexible tube to the induction apparatus' housing, which provides air flow to enable a cyclical pressurization and depressurization of the air bladder(s).

The housing includes at least one air pump (such as a miniature diaphragm pump) for inflating the air bladder, and at least one mechanical actuator (such as a solenoid valve) for deflating the air bladder. The housing can house additional pumps and valves to provide alternating positive and negative air flow, thereby both actively inflating and deflating the air bladder.

The invention overcomes several problems associated with existing motor-based erotic stimulators, such as vibrators and massagers. First, it provides stimulation that is more similar to physical touch by another human, because the air bladder can expand to a sufficient extent and with sufficient gradually changing pressure to provide stimulation without waking up the user. Also, the speed of the inflation can be made as slow as needed to achieve a sensation similar to human touch, while avoiding waking up the user. Second, this type of stimulator can be held in place above or around the user's genitalia by placing the air bladder(s) inside a pocket in a stimulation garment, such as stimulation underwear or a stimulation bra, relieving the user from the need to hold the stimulator in place. Third, the stimulator of the invention can operate silently. When stimulation is carried out during sleep using common stimulation devices, such as a vibrator, the noise created by such common stimulation devices is unacceptable, in particular when they make contact with a mattress which can act as a sound conductor. In the present invention, no motor is placed near the user, and the housing containing the pump can be completely soundproofed, connected to the air bladder(s) through a silicone tube, and conveniently stored under the user's bed.

Compared to an inflatable doll or a Fleshlight®, the present invention relieves the male user of the need to move his body or the device itself, and enables stimulation to occur during sleep, regardless of whether the male user's penis is erect or not.

One general aspect of the invention is an erotic dream induction apparatus for providing erotic stimulation to a user while the user is sleeping. The apparatus includes: a stimulation signal generator, responsive to a REM sleep onset signal, the stimulation signal generator being capable of providing a stimulation signal in response to the REM sleep onset signal; an air pump, cooperative with the stimulation signal generator, the air pump being capable of receiving the stimulation signal and providing air flow in response to the stimulation signal; and one or more inflatable air bladders, cooperative with the air pump, the one or more inflatable air bladders being capable of receiving and containing the air flow provided by the air pump; and a deflation valve, cooperative with the one or more inflatable air bladders, the deflation valve being capable of receiving the stimulation signal, and releasing air from the one or more air bladders in response to the stimulation signal, the one or more inflatable air bladders inflating and deflating in response to the air flow and the air release under control of the stimulation signal, thereby erotically stimulating the user.

In some embodiments, the REM sleep onset signal is provided by a REM sleep phase detector, the REM sleep phase detector being in sensing relationship with the user.

In some embodiments, the REM sleep phase detector is capable of analyzing a sleep phase indication so as to detect REM sleep in the user, so as to provide the REM sleep onset signal. In further embodiments, the sleep phase indication is derived from at least one of: user motion data, user EEG signals, user heart rate, and user eye movement.

In some embodiments, the air pump includes a miniature diaphragm pump.

In some embodiments, the deflation valve includes a solenoid valve.

In some embodiments, the stimulation signal generator is implemented using a micro-controller. In further embodiments, the micro-controller initiates stimulation at a particular time, or after a length of time has elapsed from reception of the REM sleep onset signal.

In some embodiments, at least one of the air bladders is housed in a pocket of a garment.

In some embodiments, at least one of the air bladders is physically embedded into a garment.

In some embodiments, at least one of the air bladders can be inserted into a vagina of the user or a rectum of the user.

In some embodiments, the stimulation is carried out while the user is sleeping, such as during a REM sleep phase.

Another general aspect of the invention is an erotic dream induction apparatus for providing erotic stimulation to a user while the user is sleeping. This apparatus includes: a REM sleep phase detector, capable of analyzing a sleep phase indication signal so as to detect REM sleep in the user, and to then provide a REM sleep onset signal; a stimulation signal generator, responsive to the REM sleep onset signal, the stimulation signal generator being capable of providing a stimulation signal in response to the REM sleep onset signal; an air pump, cooperative with the stimulation signal generator, the air pump being capable of receiving the stimulation signal and providing an air flow in response to the stimulation signal; and one or more inflatable air bladders, each air bladder being capable of being held in place against the user by a garment, each air bladder being cooperative with the air pump, each air bladder being capable of receiving and containing the air flow provided by the air pump; and a deflation valve, cooperative with the one or more inflatable air bladders, the deflation valve being capable of receiving the stimulation signal, and releasing air from the one or more air bladders in response to the stimulation signal, the one or more inflatable air bladders inflating and deflating in response to the air flow and in response to the air release under control of the stimulation signal, thereby erotically stimulating the user.

In some embodiments, the sleep phase indication is derived from at least one of: user motion data, user EEG signals, user heart rate, and user eye movement.

In some embodiments, the air pump includes a miniature diaphragm pump.

In some embodiments, the deflation valve includes a solenoid valve.

In some embodiments, the stimulation signal generator is implemented using a micro-controller, and the micro-controller initiates stimulation at a particular time or after a length of time has elapsed from reception of the REM sleep onset signal.

In some embodiments, at least one of the air bladders is wearable in a pocket of a garment worn over the user's genitalia or nipples.

In some embodiments, at least one of the air bladders is incorporated into a garment.

In some embodiments, at least one of the air bladders is shaped and sized so as to be insertable into a user's vagina or rectum.

BRIEF DESCRIPTION OF THE DRAWINGS

The invention will be more fully understood from the following detailed description, in conjunction with the following figures, wherein.

DETAILED DESCRIPTION

Figure 1A:
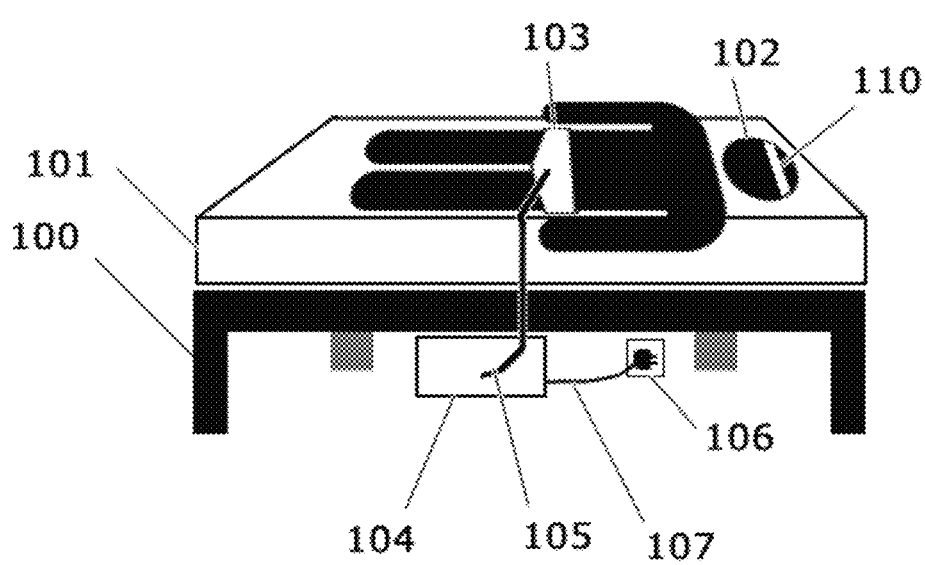
FIG. 1A is a schematic view of a user sleeping on a bed wearing a physiological monitoring headband and stimulation underwear according to the invention, also showing the housing which supplies air flow to the stimulation underwear.

FIG. 1A shows the main elements of the invention in a possible embodiment. A male user 102 is lying horizontal, supported by a bed frame 100 and a mattress 101. The user 102 is wearing stimulation underwear 103 and a physiological monitoring headband 110. Stimulation underwear 103 is underwear having at least one pocket for holding an air bladder against the male's genital area. An electrical cord 107, connected to a power outlet 106, powers the circuit board 301 and pneumatic elements inside the induction apparatus' housing 104. When the user enters the REM sleep phase, the physiological monitoring headband 110 produces a REM sleep onset signal, for instance a radio signal. The REM sleep onset signal is received by a microcontroller on the circuit board 301, housed within the apparatus' housing 104. The microcontroller produces, in response to the REM sleep onset signal, a stimulation signal. For instance, the stimulation signal could begin after a certain interval after receiving the REM sleep onset signal. Or, the stimulation signal could only be generated a number of times until the current REM phase is over.

The stimulation signal controls the action of one or more pumps and one or more valves within the housing 104. The pumps and valves provide air flow and air release to inflate and deflate air bladders 202, held within the pockets of the stimulation underwear 103, through a silicon tube 105.

Through the inflation and deflation, a cyclically varying pressure is applied to erogenous areas of the user 102, providing erotic stimulation thereto.

Figure 1B:
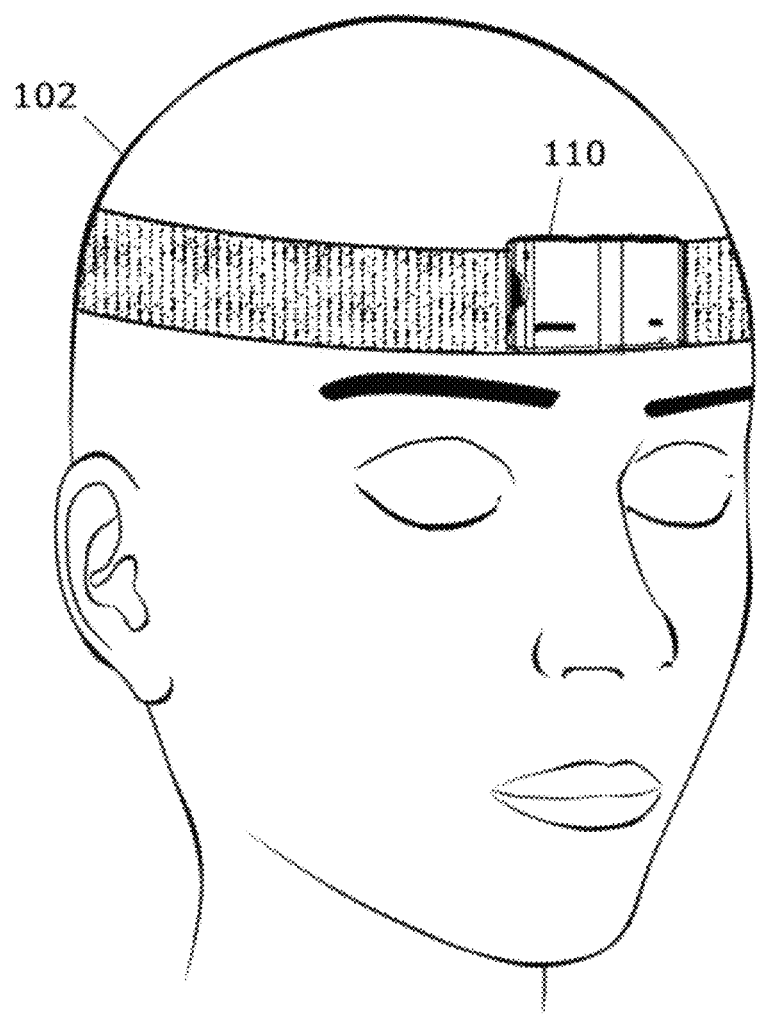
FIG. 1B is a front view of the physiological monitoring headband of FIG. 1A affixed to the user's forehead.

FIG. 1B shows the physiological monitoring headband 110 affixed to the user's 102 forehead. This is a simple way of sensing the EEG signal and detecting REM sleep. REM sleep is easily detected from the EEG signal by analyzing the frequency spectrum of the EEG signal. During REM, beta waves appear in the sleep EEG. Alternatively, REM sleep can be detected by less accurate and technically simpler methods; for instance, by monitoring eye movement with an infrared sensor, as is common in lucid dream induction masks available since the 1980s. Furthermore, in a simpler but less accurate embodiment, REM sleep can be detected by analyzing other sleep phase indications (such as noise and vibrations of the mattress 101) instead of the EEG signal; this analysis can be performed by a mobile phone app, reducing costs while also reducing accuracy.

Figure 2:
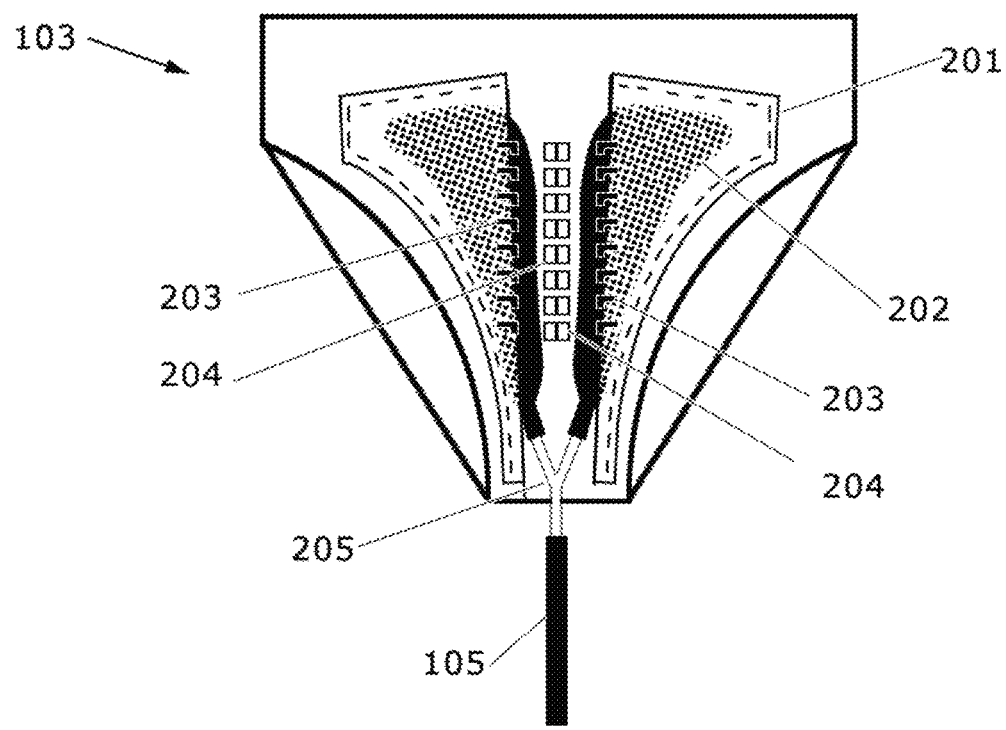
FIG. 2 is a front view of the stimulation underwear of FIG. 1A, showing two air bladders, each contained within a pocket of the stimulation underwear.

FIG. 2 shows some features of an embodiment of the stimulation underwear 103. Two non-stretchable pockets 201 are sewn on the outside of the stimulation underwear 103. The two pockets 201 each house an air bladder 202. Dashed lines indicate sewn sides of the pockets 201. The non-sewn side of each pocket is closed by means of hooks 203 and loops 204. In FIG. 2, the hooks 203 are attached to the pockets 201, and loops 204 arranged vertically and attached to the underwear 103 at its center. The pockets 201 can thus be closed like in a corset by engaging the hooks 203 with the loops 204, thereby capturing the air bladders 202 inside the pockets 201. The pockets 201 are created by sewing non-stretchable fabric on the outside of a stretchable pair of underwear. By so doing, when air is pumped into the air bladders 202, the air bladders 202 can expand only inwards towards the user's body, fully directing the pressure upon the genital area. Buttons or zippers can be substituted for the hooks 203 and loops 204 for closing the pockets 201. The two air bladders 202 are connected to the silicone tube 105 with a Y junction 205.

Figure 3:
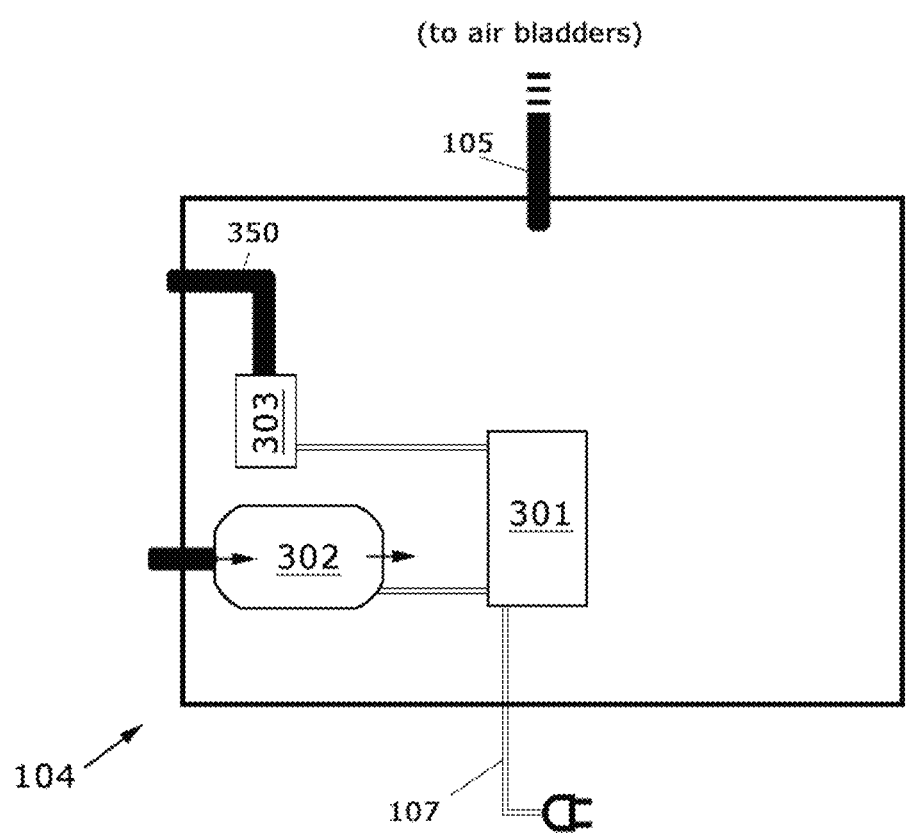
FIG. 3 is a schematic diagram of the internals of the housing of FIG. 1A, which supplies air flow to the stimulation underwear of FIG. 2 via an air tube.

FIG. 3 schematically illustrates the internals of the erotic dream induction apparatus' housing 104. In this simple embodiment, the erotic dream induction apparatus' housing 104 contains: a circuit board 301 powered through a power cord 107, a solenoid valve 303, and a miniature diaphragm pump 302. In this diagram, thick black lines represent tubing, and white lines represent electrical connections. Arrows indicate the flow of air through the pump 302 and into the airtight housing 104. A silicone tube 105 connects the space inside the airtight housing 104 to the air bladders 202 of the stimulation underwear 103 of FIG. 2. The air bladders 202 and the space inside the housing 104 are therefore always at the same pressure. When the pump 302 is not powered it impedes the flow of air in either direction. This is a common feature of miniature diaphragm pumps. When powered, the pump 302 actively moves air from the outside of the induction apparatus' housing 104 to its inside. The valve 303 allows air to pass freely in either direction if and only if it is powered; thus, when the inside of the induction apparatus' housing 104 is at higher pressure than the external environment, and the valve 303 is powered, air can escape to the outside, restoring the pressure inside the housing 104 to environmental levels. When both the pump 302 and the valve 303 are powered down, no air can flow between the inside and the outside of the airtight housing 104.

Inflation of the air bladders 202 of FIG. 2 occurs when the electronic circuitry on the circuit board 301 allows electrical current to flow to the pump 302, but not the valve 303. No air can escape through the valve duct 350 (because the valve 303 is powered down). Pressure inside the housing 104 increases due to the action of the pump, and the air bladders 202, connected through the silicone tube 105 to the pressurized interior of the housing 104, inflate.

Conversely, deflation of the air bladders 202 is accomplished when the circuitry on the circuit board 301 powers down the pump 302, but allows current to flow to the valve 303, thereby allowing airflow through it. Under these conditions, the pump 302 resists air movement in either direction. Pressure inside the housing 104 falls because air escapes through the valve, to the valve duct 350 and ultimately to the outside of the housing 104. The air bladders 202 deflate as a result of the outflow of air.

Figure 4:
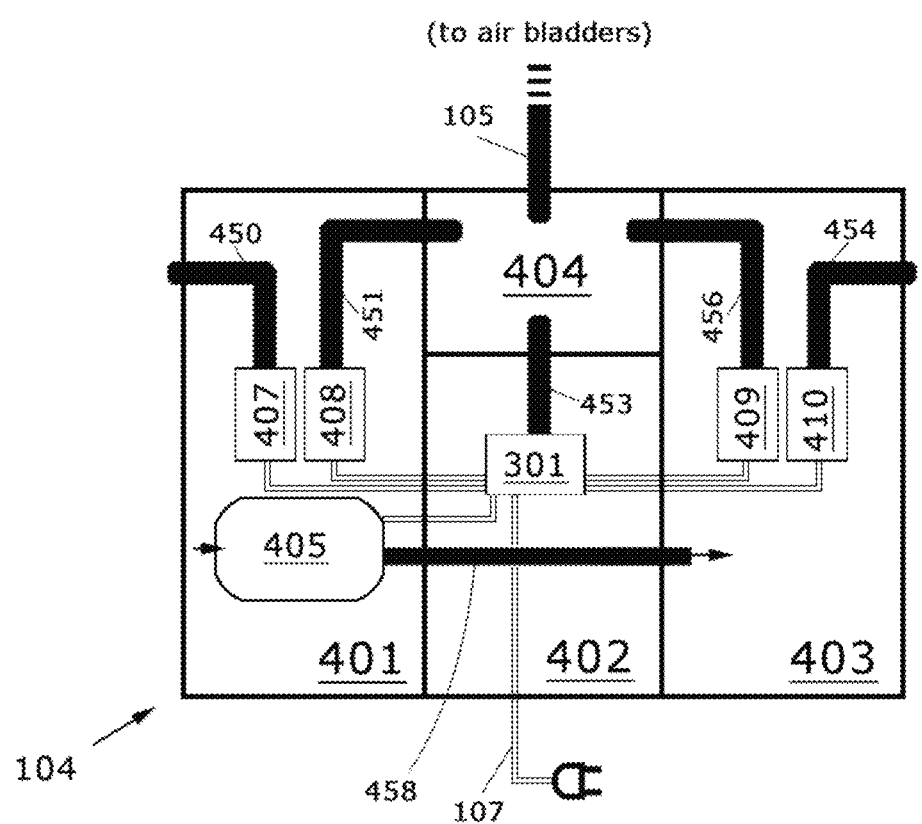
FIG. 4 is a schematic diagram of the internals of a housing having a more complex air reservoir, which enables stronger stimulation.

FIG. 4 illustrates a more complex embodiment allowing the induction apparatus to inflate and deflate the air bladders 202 more quickly, thus achieving stronger stimulation. This embodiment utilizes a plurality of valves (a negative pressure outlet valve 407, a negative pressure inlet valve 408, a positive pressure outlet valve 410, and a positive pressure inlet valve 409). It also utilizes a plurality of air compartments within the housing 104. In the embodiment of FIG. 4, the induction apparatus' housing 104 is divided into four different air-tight compartments (a negative pressure compartment 401, a circuitry compartment 402 housing the circuit board 103, a positive pressure compartment 403, and a central compartment 404). The central compartment 404 is always at equal pressure with the air bladders 202 shown in FIG. 2, to which it is connected via the silicone tube 105. Air cannot move between compartments except through conduits or tubing, shown in the picture as thick black lines. The flow of air between the various compartments and the outside of the housing 104 will be explained. In this explanation the word "connected" is meant to indicate that flow of air is possible. The negative pressure compartment 401 is connected to the outside by means of a negative pressure inlet valve 407 and a negative pressure inlet duct 450. Only when the negative pressure inlet valve 407 is powered on, air can flow (in both directions) between the negative pressure compartment 401 and the outside of the enclosure. The negative pressure compartment 401 is connected to the central compartment 404 by means of a negative pressure outlet valve 408 and a negative pressure outlet duct 451. Only when the negative pressure outlet valve 408 is powered on, air can flow (in both directions) between the negative pressure compartment 401 and the central compartment 404. The positive pressure compartment 403 is connected to the outside by means of a positive pressure inlet valve 410 and a positive pressure inlet duct 454. Only when the positive pressure inlet valve 410 is powered on, air can flow (in both directions) between the positive pressure compartment 403 and the space outside of the enclosure. The positive pressure compartment 403 is connected to the central compartment 404 by means of a positive pressure outlet valve 409 and a positive pressure outlet duct 456. Only when the positive pressure outlet valve 409 is powered on, air can flow (in both directions) between the positive pressure compartment 403 and the central compartment 404. A central compartment pressure sensing tube 453 connects the central compartment 404 to a pressure sensor mounted on the circuit board 301 in the circuitry compartment 402. However, the circuitry compartment 402 and the central compartment 404 are not pneumatically connected, and air never flows between them. When powered on, the diaphragm pump 405 moves air from the negative pressure compartment 401 to the positive pressure compartment 403; this air movement is indicated by the arrows entering 405 and exiting 458. When the pump 405 is powered off, no air can flow between the negative pressure compartment 401 and the positive pressure compartment 403.

When all valves and pumps are powered down, no air flows between any of the compartments. The air bladders 202 and the central compartment 404 are at equal pressure as they are connected through a silicone tube 105 with no valve. The pressures in the negative pressure compartment 401 and the positive pressure compartment 403 are unknown. Pressure in the circuitry compartment 402 is irrelevant as it is not part of the pneumatic system; in fact this compartment is not strictly required for the pneumatic functioning of the device but simply houses the necessary circuitry.

To inflate the air bladders 202 at regular speed (achieving an inflation and deflation speed of which the embodiment of FIG. 3 is also capable), two of the valves (the negative pressure inlet valve 407 and positive pressure outlet valve 409), and the pump 405 are powered by the circuitry on the circuit board 301. All other pneumatic elements are powered down. Air flows from the outside of the housing through negative pressure inlet duct 450 and negative pressure inlet valve 407, moved by the action of the pump 405. Air flows from the negative pressure compartment 401 to the positive pressure compartment 403 through a conduit 458. Air continues to flow from the positive pressure compartment 403 to the positive pressure outlet valve 409, then to the positive pressure outlet duct 456, on to the central compartment 404 and finally through a silicone tube 105 to the air bladders 202, thereby inflating them.

Conduit 458 allows air to be moved by the diaphragm pump 405, from the negative pressure compartment 401 into the positive pressure compartment 403, although the pump itself resides entirely within the negative pressure compartment 401. Many miniature diaphragm pumps have a discharge nozzle to which a silicone tube can be connected, but no similar nozzle on the suction side; for this reason the diaphragm pump 405 is located in the negative pressure compartment so as to enable air to be suctioned from of this compartment.

To deflate the air bladders 202 at regular speed (no different from the embodiment of FIG. 3), the negative pressure outlet valve 408 and negative pressure inlet valve 407 are powered. All other pneumatic elements are powered down. Air escapes freely from the central compartment 404 through the negative pressure outlet duct 451, the negative pressure outlet valve 408, the negative pressure inlet valve 407 and the negative pressure inlet duct 450 (in sequence) to the outside of the enclosure 104. The same effect can be obtained by opening the positive pressure outlet valve 409 and the positive pressure inlet valve 410 instead. Air then flows in this sequence: air bladders 202, silicone tube 105, central compartment 404, positive pressure outlet duct 456, positive pressure outlet valve 409, positive pressure inlet valve 410, positive pressure inlet duct 454, to the outside of the enclosure 104. If all four valves are powered on, air can leave the interior of the enclosure 104 and be discharged into the environment slightly faster, reducing the time required to completely deflate the air bladders 202.

The inflation and deflation speed increase ("boost") in the embodiment of FIG. 4 is realized when pressure is allowed to accumulate in the compartments prior to any air moving into or out of the air bladders 202. To rapidly inflate the air bladders 202, positive pressure is first built in the positive pressure compartment 403 (step 1). To accomplish this, the negative pressure inlet valve 407 and the pump 405 are turned on. Air moves from the outside of the enclosure through the negative pressure inlet duct 450, the negative pressure inlet valve 407, the pump 405, into the positive pressure compartment 403. Pressure builds inside the positive pressure compartment 403 as both valves in the positive pressure compartment are powered down and there is no way for the air to escape. After a certain interval, to rapidly inflate the air bladders 202, the negative pressure inlet valve 407 is closed, the pump 405 is powered down, and the positive pressure outlet valve 409 is opened (step 2). When this occurs the air accumulated inside the positive pressure compartment 403 rushes into the air bladders through the positive pressure outlet duct 456, at a rate much faster than a miniature diaphragm pump can move air. The speed increase is directly proportional to the size of the positive pressure compartment 403, the length of step 1 and the type of pump used. It is to be noted that the size of the pump used is limited not only by cost and space considerations, but also by the noise produced which may disturb, and perhaps awaken the user.

To rapidly deflate the air bladders 202, first air must be suctioned out of the negative pressure compartment 401, so as to reduce its pressure to a level below that of the environment outside the enclosure 104. To accomplish this, the circuitry on the circuit board 301 powers the pump 405 and the positive pressure inlet valve 41. All other elements are powered down. Air is moved from the negative pressure compartment 401 into the positive pressure compartment 403 by the pump 405; and air is allowed to escape through the positive pressure inlet valve 410 and positive pressure inlet duct 454. The positive pressure compartment 403 maintains constant pressure with the environment outside the housing, but more and more air is moved out of the negative pressure compartment 401. Pressure in the negative pressure compartment 401 falls. After a certain interval, the pump 405 and the positive pressure inlet valve 410 are powered down, and the negative pressure outlet valve 408 is opened. Air rushes out of the air bladders 202 through the central compartment 404, the negative pressure outlet duct 451 and the negative pressure outlet valve 408 into the negative pressure compartment 401. In this manner the air bladders 202 are deflated rapidly. The speed of deflation is directly proportional to the degree to which the pressure inside the negative pressure compartment 401 can be lowered with respect to the air in the air bladders 202 prior to opening the negative pressure outlet valve 408.

The noise produced by the diaphragm pump in any of the embodiments described can be reduced by choosing an appropriately thick enclosure. For example, a 1 cm thick polycarbonate enclosure can completely silence the noise created by a miniature diaphragm pump of the kind required to practice the present invention.

Figure 5:
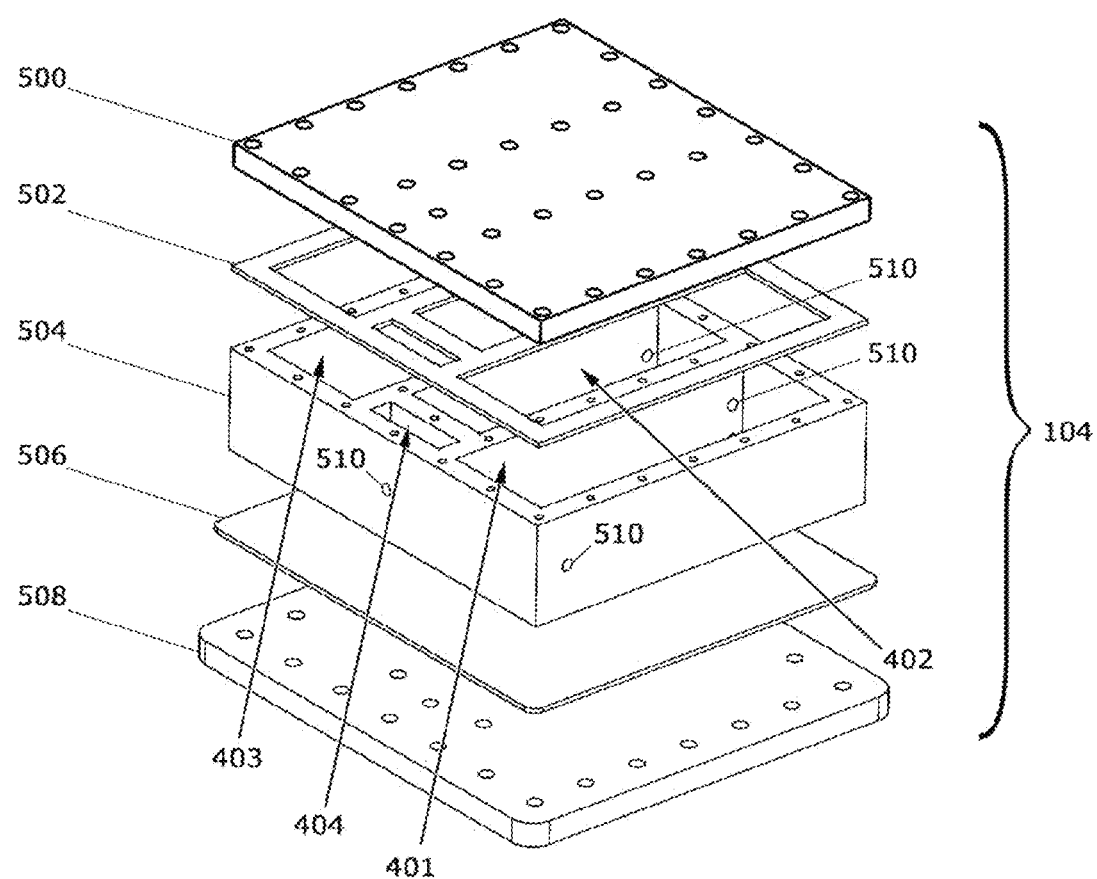
FIG. 5 is an exploded view of the housing of FIGS. 3 and 4, showing the structural elements.

Air-proofing is essential to practicing the present invention. In FIG. 5, the structural elements of the induction apparatus' housing 104 are shown. This structural configuration minimizes manufacturing costs and allows reliable air-proofing. This embodiment of the housing 104 allows the realization of the induction apparatus embodiment of FIG. 4. For ease of reference to FIG. 4, the air compartments are labeled with arrows.

A rubber mat 506 is captured between a plastic base 508 and a plastic mid-section 504. A rubber gasket 502 is captured between the plastic mid-section 504 and a plastic top 500. The plastic base 508 and the plastic top 500 have a large number of screw holes through which screws are inserted at assembly time. The screws penetrate the walls of the mid-section, ensuring that the rubber mat 506 and rubber gasket 502 are well compressed at every location. This is important to ensure that air cannot leak out of the housing 104 when the air pressurized. All unlabeled holes on the plastic mid-section 504 are screw holes. All holes on the plastic base 508 and plastic top 500 are screw holes.

In FIG. 5, several cabling and tubing holes 510 on the plastic mid-section 504 allow cabling or tubes to penetrate the enclosure walls, to achieve the internal configuration and functionality previously explained in reference to FIG. 4. Rubber grommets are inserted in the cabling and tubing holes 510 for air-proofing.

The rubber gasket 502 can easily be replaced by another rubber mat 506, as their function is identical.

Figure 6:
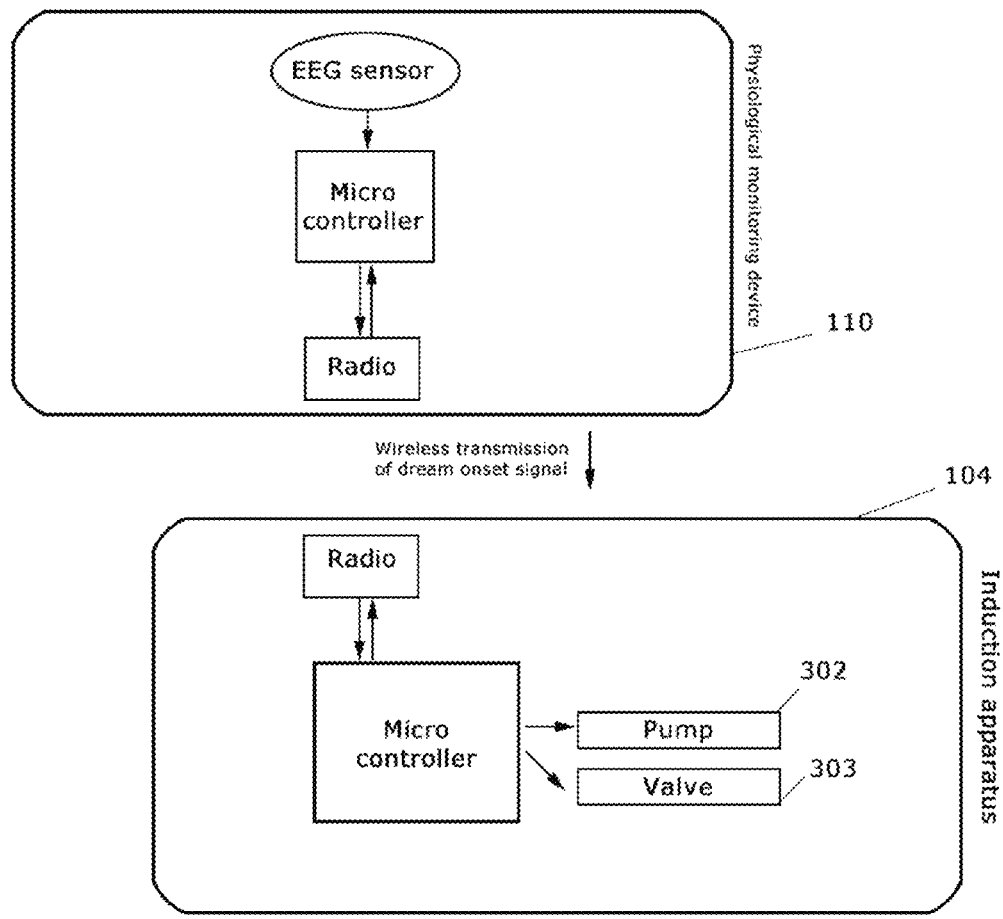
FIG. 6 is a block diagram of the components of the physiological monitoring headband and the housing of FIG. 3.

FIG. 6 schematically represents the intercommunication and components of the physiological monitoring headband 110 (having an EEG sensor in communication with a microcontroller that is cooperative with a radio transceiver), and the induction apparatus' housing 104 (having a radio transceiver for communicating with the radio transceiver of the headband 110, a microcontroller cooperative with the radio transceiver, the microcontroller also controlling the pump 302 and the valve 303, consistent with the embodiment of FIG. 3.

Other modifications and implementations will occur to those skilled in the art without departing from the spirit and the scope of the invention as claimed. Accordingly, the above description is not intended to limit the invention, except as indicated in the following claims.

What is claimed is:

1. An erotic dream induction apparatus for providing erotic stimulation to a user while the user is sleeping, the apparatus comprising:
   a stimulation signal generator, responsive to a REM sleep onset signal, the stimulation signal generator being capable of providing a stimulation signal in response to the REM sleep onset signal;
   an air pump, cooperative with the stimulation signal generator, the air pump being capable of receiving the stimulation signal and providing air flow in response to the stimulation signal;
   a sound-proof housing enclosing the air pump, the sound-proof housing being configured to enable the air pump to operate substantially silently;
   one or more inflatable air bladders, cooperative with the air pump, the one or more inflatable air bladders being capable of receiving and containing the air flow provided by the air pump; and
   stimulation underwear having one or more pockets for holding the one or more inflatable air bladders against a genital area of the user; and
   a deflation valve, cooperative with the one or more inflatable air bladders, the deflation valve being capable of receiving the stimulation signal, and releasing air from the one or more air bladders in response to the stimulation signal,
   the one or more inflatable air bladders inflating and deflating in response to the air flow and the air release under control of the stimulation signal, thereby erotically stimulating the user.

2. The apparatus of claim 1, wherein the REM sleep onset signal is provided by a REM sleep phase detector, the REM sleep phase detector being in sensing relationship with the user.

3. The apparatus of claim 2, wherein the REM sleep phase detector is capable of analyzing a sleep phase indication so as to detect REM sleep in the user, so as to provide the REM sleep onset signal.

4. The apparatus of claim 3, wherein the sleep phase indication is derived from at least one of:
   user motion data, user EEG signals, user heart rate, and user eye movement.

5. The apparatus of claim 1, wherein the air pump includes a miniature diaphragm pump.

6. The apparatus of claim 1, wherein the deflation valve includes a solenoid valve.

7. The apparatus of claim 1, wherein the stimulation signal generator is implemented using a micro-controller.

8. The apparatus of claim 7, wherein the micro-controller initiates stimulation at a particular time, or after a length of time has elapsed from reception of the REM sleep onset signal.

9. The apparatus of claim 1, wherein at least one of the air bladders is housed in the one or more pockets.

10. The apparatus of claim 1, wherein at least one of the air bladders is physically embedded into the stimulation underwear.

11. The apparatus of claim 1, wherein at least one of the air bladders can be inserted into a vagina of the user or a rectum of the user.

12. The apparatus of claim 1, wherein the stimulation is carried out while in a REM sleep phase.

13. An erotic dream induction apparatus for providing erotic stimulation to a user while the user is sleeping, the apparatus comprising:
   a REM sleep phase detector, capable of analyzing a sleep phase indication signal so as to detect REM sleep in the user, and to then provide a REM sleep onset signal;
   a stimulation signal generator, responsive to the REM sleep onset signal, the stimulation signal generator being capable of providing a stimulation signal in response to the REM sleep onset signal;
   an air pump, cooperative with the stimulation signal generator, the air pump being capable of receiving the stimulation signal and providing an air flow in response to the stimulation signal;
   a sound-proof housing enclosing the air pump, the sound-proof housing being configured to enable the air pump to operate substantially silently; and
   one or more inflatable air bladders, each air bladder being capable of being held in place against only a genital area of the user by a garment, each air bladder being cooperative with the air pump, each air bladder being capable of receiving and containing the air flow provided by the air pump; and
   a deflation valve, cooperative with the one or more inflatable air bladders, the deflation valve being capable of receiving the stimulation signal, and releasing air from the one or more air bladders in response to the stimulation signal,
   the one or more inflatable air bladders inflating and deflating in response to the air flow and in response to the air release under control of the stimulation signal, thereby erotically stimulating the user.

14. The apparatus of claim 13, wherein the sleep phase indication signal is derived from at least one of:
   user motion data, user EEG signals, user heart rate, and user eye movement.

15. The apparatus of claim 13, wherein the air pump includes a miniature diaphragm pump.

16. The apparatus of claim 13, wherein the deflation valve includes a solenoid valve.

17. The apparatus of claim 13, wherein the stimulation signal generator is implemented using a micro-controller, and the micro-controller initiates stimulation at a particular time or after a length of time has elapsed from reception of the REM sleep onset signal.

18. The apparatus of claim 13, wherein at least one of the air bladders is wearable in a pocket of a garment worn over the user's genitalia or nipples.

19. The apparatus of claim 13, wherein at least one of the air bladders is incorporated into a garment.

20. The apparatus of claim 13, wherein at least one of the air bladders is shaped and sized so as to be insertable into a user's vagina or rectum.

* * * * *